US 008506503B2

(12) United States Patent
Fritscher-Ravens et al.

(10) Patent No.: US 8,506,503 B2
(45) Date of Patent: Aug. 13, 2013

(54) SYSTEM AND METHOD FOR PERFORMING A FULL THICKNESS TISSUE BIOPSY

(75) Inventors: Annette Fritscher-Ravens, Bruchhausen-Vilsen (DE); Vihar C. Surti, Winston-Salem, NC (US); Charles W. Agnew, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 265 days.

(21) Appl. No.: 12/914,608

(22) Filed: Oct. 28, 2010

(65) Prior Publication Data
US 2011/0105947 A1    May 5, 2011

Related U.S. Application Data

(60) Provisional application No. 61/256,664, filed on Oct. 30, 2009.

(51) Int. Cl.
*A61B 10/00* (2006.01)
(52) U.S. Cl.
USPC .......................................................... 600/567
(58) Field of Classification Search
USPC ................................ 600/562–567; 606/110
See application file for complete search history.

(56) References Cited

U.S. PATENT DOCUMENTS

| 3,929,123 | A | * | 12/1975 | Jamshidi ........................ 600/567 |
| 5,040,542 | A | | 8/1991 | Gray |
| 5,353,804 | A | | 10/1994 | Kornberg et al. |
| 5,538,010 | A | | 7/1996 | Darr et al. |
| 6,899,685 | B2 | | 5/2005 | Kermode et al. |
| 7,189,207 | B2 | | 3/2007 | Viola |
| 7,419,472 | B2 | | 9/2008 | Hibner et al. |
| 2004/0153003 | A1 | | 8/2004 | Cicenas et al. |
| 2006/0116605 | A1 | | 6/2006 | Nakao |
| 2007/0118049 | A1 | | 5/2007 | Viola |
| 2007/0255174 | A1 | | 11/2007 | Hibner |
| 2010/0049087 | A1 | * | 2/2010 | Spero et al. .................... 600/567 |
| 2010/0145352 | A1 | * | 6/2010 | Chang et al. .................. 606/110 |

FOREIGN PATENT DOCUMENTS

| WO | WO 02/065919 A1 | 8/2002 |
| WO | WO 2007/098354 A1 | 8/2007 |
| WO | WO 2007/134100 A2 | 11/2007 |

OTHER PUBLICATIONS

International Search Report dated Jan. 20, 2011, issued in related International Patent Application No. PCT/US2010/054297.

* cited by examiner

*Primary Examiner* — Brian Szmal
(74) *Attorney, Agent, or Firm* — Brinks, Hofer, Gilson & Lione

(57) ABSTRACT

A medical system for performing a tissue biopsy at a remote location within a patient is disclosed. The medical system comprises an elongate outer cutting member, an elongate inner member movably disposed within the outer member, and a tissue traction member for anchoring bodily tissue and pulling a sample of the tissue within the outer cutting member.

22 Claims, 10 Drawing Sheets

SYSTEM AND METHOD FOR PERFORMING A FULL THICKNESS TISSUE BIOPSY

PRIORITY CLAIM

This application claims the benefit of U.S. Provisional Application 61/256,664, entitled "System and Method for Performing a Full Thickness Tissue Biopsy," filed Oct. 30, 2009, the disclosure of which is hereby incorporated by reference in its entirety.

FIELD OF THE INVENTION

The present invention relates generally to medical systems, and more particularly to medical systems and methods for performing a tissue biopsy.

BACKGROUND OF THE INVENTION

Biopsy is the removal and study of body tissue for medical diagnosis. Physicians in many specialties commonly obtain biopsy samples of a target tissue area from patients in order to detect abnormalities such as cancer. When physicians must access a biopsy location inside a patient's abdominal cavity, thoracic cavity, or gastro-intestinal system, an invasive procedure is necessary. For such procedures, physicians often use an endoscope to avoid more traumatic open surgery. Generally, modern endoscopes are long flexible instruments having a light source and an image sensor for visualizing the interior of an internal region of the body. In addition, endoscopes commonly have an accessory or working channel though which another device, such as a biopsy device or a tissue anchor delivery device, can be advanced toward the target area. Alternatively, an external accessory channel may accompany and be used with an endoscope.

When a medical professional wishes to obtain a cellular tissue biopsy sample, one common procedure he or she may perform is fine needle aspiration, or FNA. Aspiration is a suction process that removes a tissue sample that is suitable for examination under a microscope. Generally, a hollow fine gauge needle engages the tissue and a syringe or comparable device sucks the tissue sample through the needle or needle system by creating a negative pressure between the syringe and the sample. Various types of hollow needles are used in an aspiration biopsy to obtain the tissue sample, such as a beveled needle, a ball-tipped needle, or a dimpled needle. U.S. Patent Publication No. 2006/0116605 discloses a needle having a spoon-shaped configuration in which rotational movement of the needle scoops a sample of the tissue during aspiration.

Biopsy devices configured for an FNA procedure generally further include an outer sheath containing a sheath lumen in which the needle is slidably disposed. The sheath protects outer surroundings, such as the working channel of the endoscope, from the sharp end of the needle as the biopsy device is advanced toward the target area. During advancement of the device, the needle remains completely within the sheath. At the target area, the distal end of the needle extends beyond the outer sheath to pierce the tissue and obtain a sample. The needle retracts inside the sheath after the sample is taken.

When obtaining a tissue sample that is larger than a cellular sample is desired, it may not be preferred to use an FNA procedure. Rather, a biopsy system that comprises a cutting cannula and stylet assembly may be used. The system is operated using a spring-loaded handle of the type disclosed in U.S. Pat. No. 5,538,010, the disclosure of which is incorporated herein by reference. Another biopsy instrument utilizing a stylet and cannula assembly is the QUICK-CORE™ Biopsy Set, manufactured by Cook, Inc., Bloomington, Ind. The inner part or stylet has a sample collecting element or notch formed near a stylet distal end. The distal end of the stylet is driven into the target area, and the tissue prolapses into the sample collecting notch. Thereafter, a spring-loaded cutting cannula is rapidly advanced distally into the underlying tissue and thereby cuts the portion of the tissue disposed in the collecting notch. After the sample is cut, the stylet with the retained sample and the cannula covering the stylet are retracted from the target area.

Although the biopsy systems having a collecting notch are used to obtain tissue samples that are larger than cellular samples, such tissue samples are still of limited depth. Also, the tissue samples must be taken from the side. As a result, displacement of the tissue sample may occur when retracting the stylet. Thus, there exists a need to obtain deep core samples taken straight on, and there exists a need for a more secure attachment of the sample. Additionally, the stylet and cutting cannula of these biopsy systems are both configured to pierce, shear, or cut tissue. Unlike the outer sheath of the biopsy device configured for the FNA procedure, the outer cutting cannula does not function as an adequate sheath and can damage the working channel of the endoscope or bodily tissue. Thus, there exists a need to protect the outer surroundings from the cutting edge of the cannula.

BRIEF SUMMARY OF THE INVENTION

The present invention provides medical systems and related methods for performing a tissue biopsy. The system comprises an elongate outer cutting member having a cutting edge circumferentially disposed about a distal end thereof, an elongate inner member movably disposed within the outer cutting member, and a tissue traction mechanism movably disposed within the inner member. In an exemplary embodiment, the outer cutting member and the inner member comprise a biopsy device. The biopsy device may be utilized with a number of various tissue traction mechanisms.

The biopsy system may be used in conjunction with an endoscope. For example, the endoscope may comprise a working channel through which the biopsy system may be advanced toward a target tissue area. To reduce contact between the cutting edge of the biopsy system and an interior surface of the working channel, the cutting edge may comprise an inwardly slanted bevel, wherein the cutting edge is disposed adjacent the outer surface of the inner member. To further reduce contact between the cutting edge and the interior surface of the working channel, a protective cap disposed on a distal end of the inner member may be positioned at a first position extending distally beyond the cutting edge. The biopsy device is generally movable between the first position and a second position retracted within the outer cutting member. To obtain the biopsy sample, the protective cap is withdrawn from the first position to the second position.

The biopsy system may include a handle member comprising a first handle portion fixedly connected to the outer cutting member, and a second handle portion fixedly connected to the inner member. The first handle portion and the second handle portion may move relative to each other to enable movement of the protective cap between the first and second positions.

The biopsy system may include various embodiments of the tissue traction mechanism. Generally, the tissue traction mechanism comprises a mechanical tissue anchor in connection with an operating member. In one embodiment, the tissue traction mechanism may comprise a tissue anchor attached to a suture. In another embodiment, the tissue traction mechanism may comprise a stylet having a distal tip configured for piercing and anchoring the tissue. One type of distal tip may comprise a corkscrew configuration. Another type of distal tip may comprise a barbed configuration.

A method for performing a tissue biopsy at a target area is also provided in accordance with the teachings of the present invention. The biopsy device is advanced toward the target area. During advancement, the protective cap is in the first position so as to prevent the cutting member from causing damage to an introducer and/or the patient. Once at the biopsy site, the protective cap in the first position engages with the tissue. The tissue traction mechanism is then advanced to engage the tissue. The tissue is anchored. Then, the protective cap is retracted relative to the outer cutting member toward the second position so as to expose and engage the cutting edge with the tissue. The cutting member is rotated and distally advanced while proximally pulling the anchored tissue until a tubular sample is detached from the underlying tissue.

DETAILED DESCRIPTION OF THE INVENTION

Figure 1A:
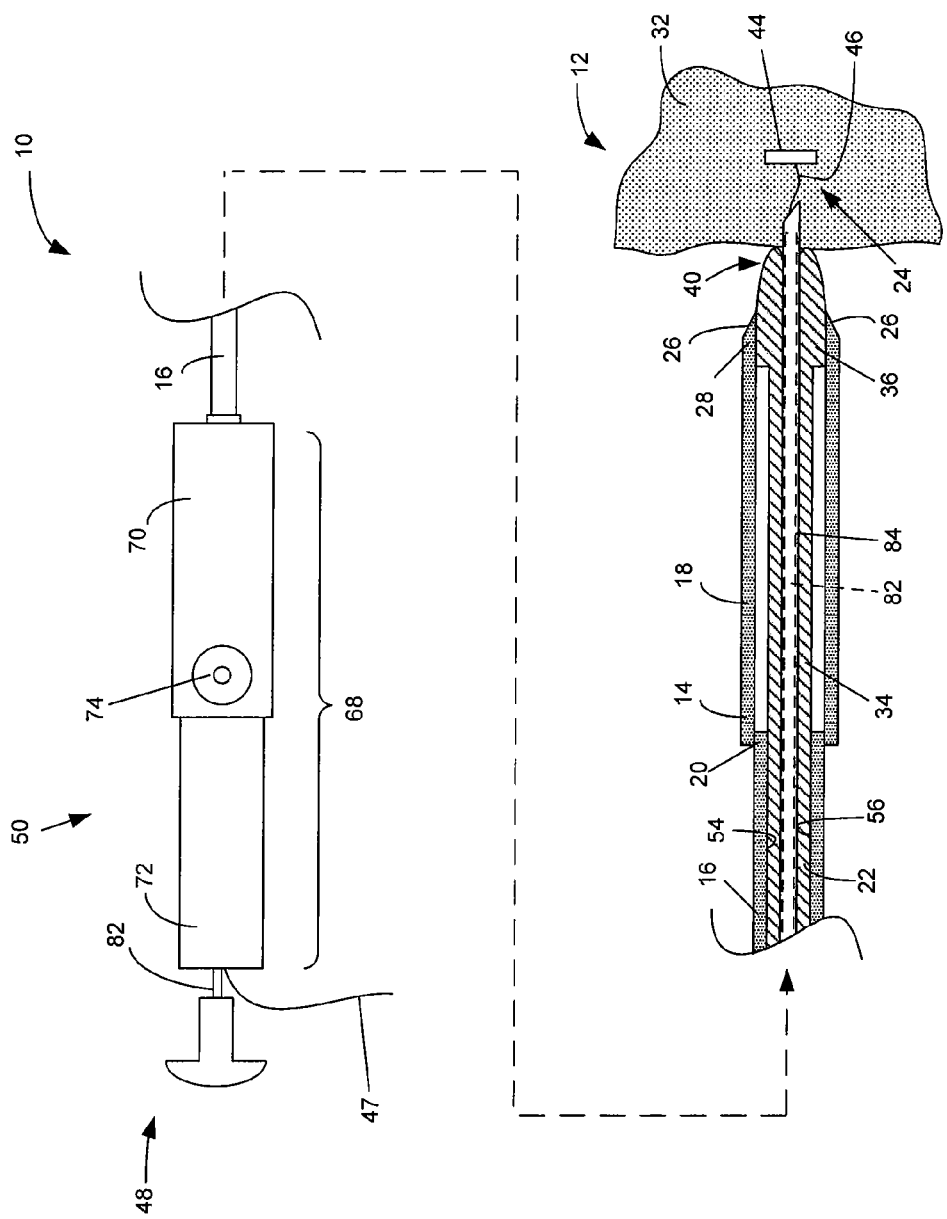
FIG. 1A is a side view of the medical biopsy system, partially in cross-section, showing a slidable disposition between the outer member and the inner member, where the protective cap is positioned in the first position and engaged with the tissue, where the tissue traction mechanism includes a tissue anchor and a suture, and where the tissue anchor is anchored into the tissue.
Figure 1B:
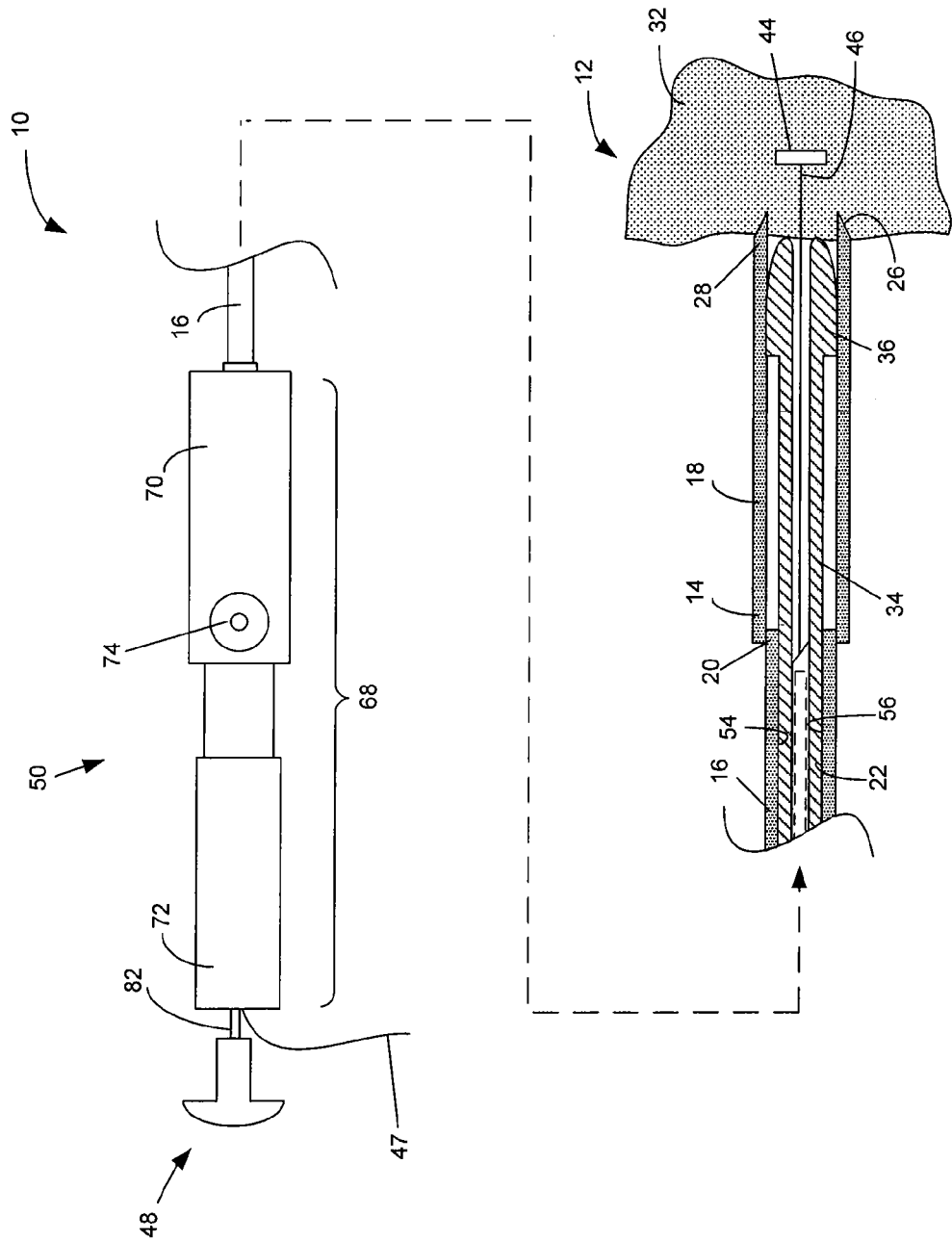
FIG. 1B is a side view of the system shown in FIG. 1A, illustrating the cutting member engaged with the tissue.
Figure 1C:
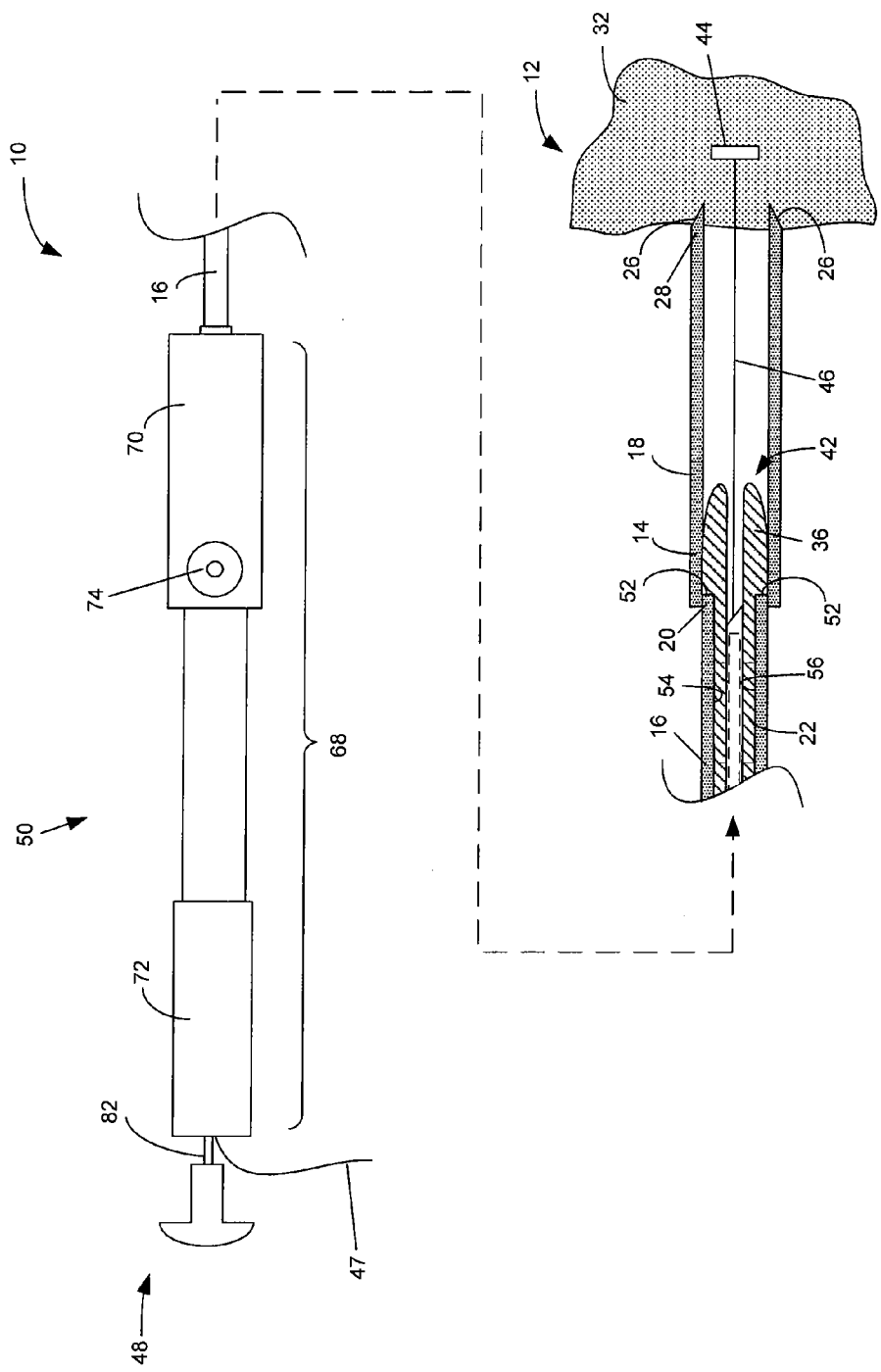
FIG. 1C is a side view of the system shown in FIG. 1A, illustrating the protective cap positioned in the second position.
Figure 1D:
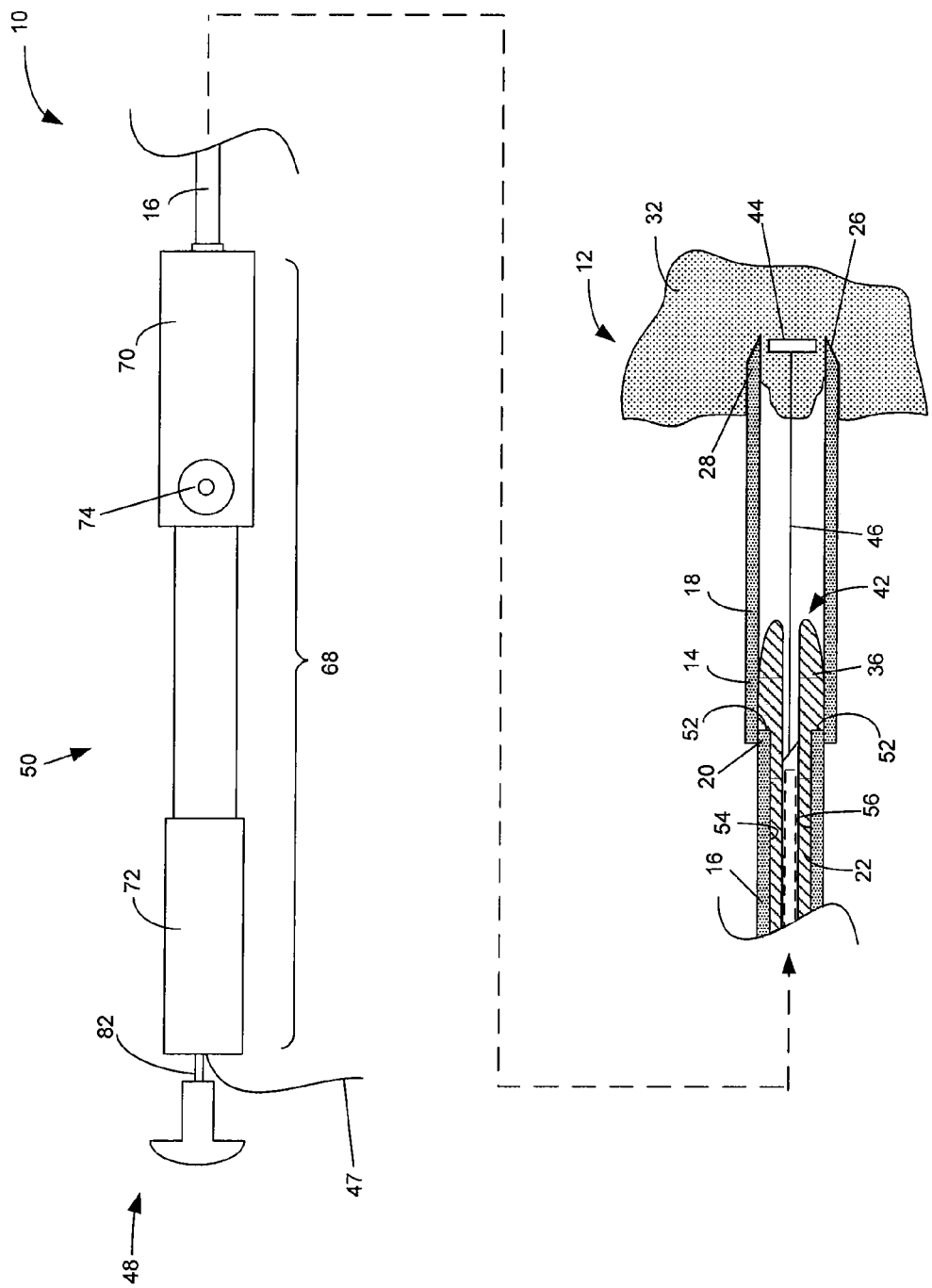
FIG. 1D is a side view of the system shown in FIG. 1A, illustrating the tissue traction mechanism withdrawn so as to apply traction to the tissue, and the cutting member advanced into the tissue.
Figure 1E:
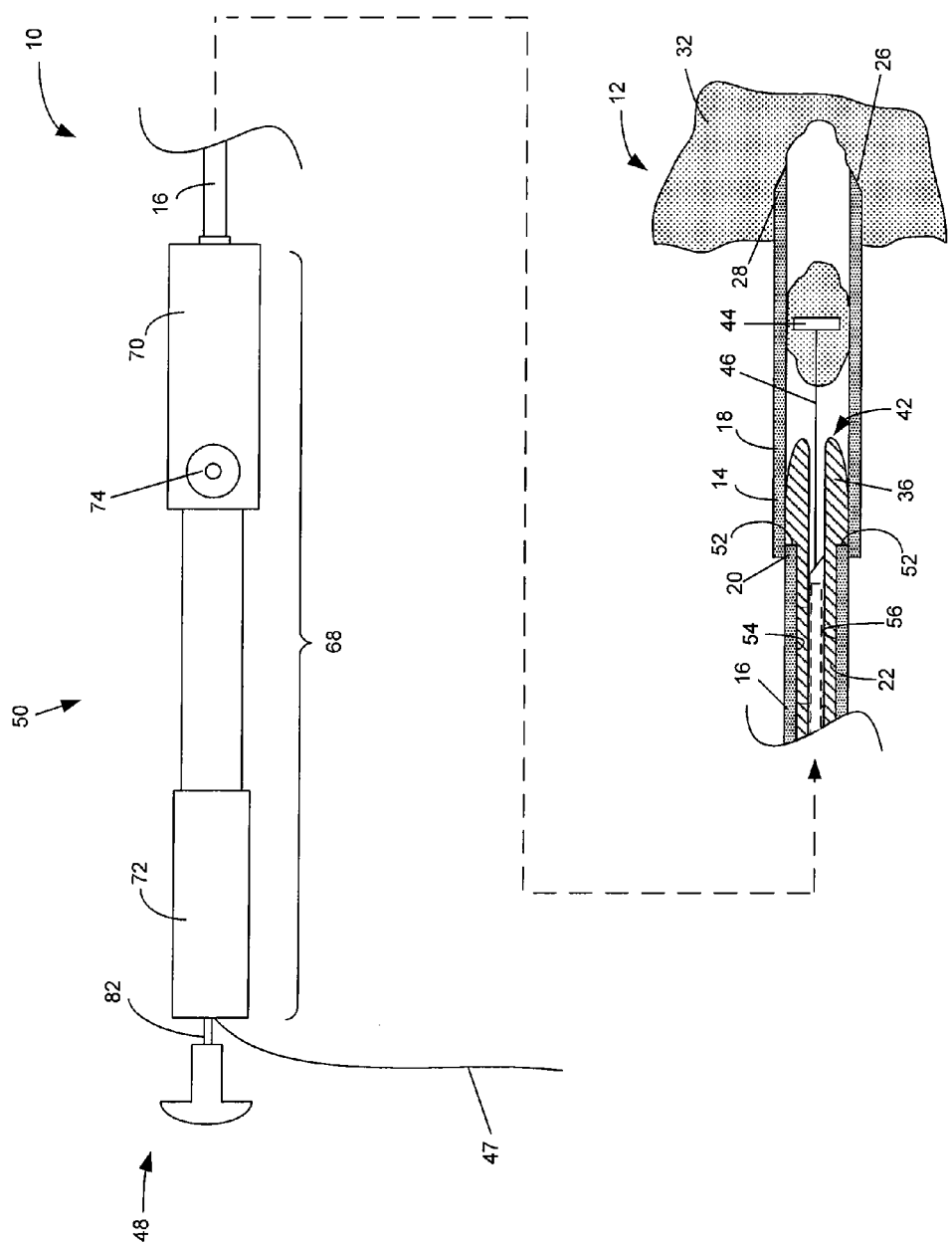
FIG. 1E is a side view of the system shown in FIG. 1A, illustrating the tubular tissue sample torn from the tissue and within the cutting member.

FIGS. 1A-1E illustrate various configurations of a medical biopsy system 10 for performing a tissue biopsy at a target area 12 within a patient. The medical biopsy system 10 comprises an elongate outer member 14 comprising an elongate torsion shaft 16 and a tubular cutting member 18 disposed on a distal portion 20 of the torsion shaft 16, an elongate inner member 22 movably disposed within the outer member 14, and a tissue traction mechanism 24 movably disposed within the inner member 22. The cutting member 18 includes a cutting edge 26 circumferentially disposed about a distal end 28 thereof. The cutting edge 26 is configured to engage and cut out a tubular tissue sample 30 from underlying tissue 32 upon rotation and distal advancement of the torsion shaft 16. The inner member 22 comprises a shaft portion 34 having a protective cap 36 disposed on a distal end 38 thereof. The protective cap 36 is movable between a first position 40 extending distally beyond the cutting edge 26 and a second position 42 retracted within the cutting member 18. The tissue traction mechanism 24 comprises a mechanical tissue anchor 44 connected to an operating member 46. A proximal end 47 of the operating member 46 extends to near a proximal end 48 of the medical biopsy system 10. As shown in FIGS. 1D and 1E, the tissue traction mechanism 24 is configured to engage and pull the tubular tissue sample 30 into the cutting member 18.

The outer member 14 and the inner member 22 comprise a biopsy device 50, and the biopsy device 50 together with the tissue traction mechanism 24 comprises the medical biopsy system 10. That is, the medical biopsy system 10 may be utilized with a number of different tissue traction mechanisms 24, and therefore the biopsy device 50 may be provided separately such that a medical professional operating the device may utilize tissue traction mechanisms 24 of his or her own choosing. At the same time, the biopsy device 50 may be also provided with a tissue traction mechanism 24, thereby forming the medical biopsy system 10 in accordance with the teachings of the present invention.

FIG. 1A illustrates the biopsy device 50 where the protective cap 36 is positioned in the first position 40. When the biopsy device 50 is being delivered to the target area 12, the protective cap 36 is in the first position 40 extending distally beyond the cutting edge 26. In the first position 40, the protective cap 36 prevents outside surroundings, such as bodily structures or the inside of an endoscope, from being damaged by the sharp cutting edge 26 of the cutting member 18. In the first position 40, the protective cap 36 also prevents the cutting edge 26 from engaging with and cutting the underlying tissue 32.

As shown in FIGS. 1B-1D, when the biopsy device 50 is in position to obtain a tubular sample of tissue 30, the protective cap 36 is in the second position 42, retracted within the cutting member 18. When the protective cap 36 is in the second position 42, the cutting edge 26 is exposed and may engage with and cut the tissue 32. As shown in FIGS. 1C-1E, an outer diameter of the protective cap 36 may be larger than an inner diameter of the torsion shaft 16, preventing the protective cap 36 from being retracted into the torsion shaft 16. In this configuration, the second position 42 is at a proximal portion 52 of the cutting member 18 abutting the distal portion of the torsion shaft 20.

In one embodiment of the biopsy system 10, shown in FIGS. 1A-1E, the inner member 22 is slidably disposed within the outer member 12. In this embodiment, an inner surface 54 of the outer member 14, and an outer surface 56 of the inner member 22 are each uniformly and substantially smooth, such that when either the outer member 14 or the inner member 22 is biased relative to the other by a force applied in an axial direction, the biased member moves relative to the non-biased member in the axial direction. Depicted in FIGS. 1B-1E, when a proximal force is applied to the inner member 22 relative to the outer member 14, the inner member 22 proximally moves relative to the outer member 14. Likewise, when a distal force is applied to the outer member 14 relative to the inner member 22, the outer member 14 moves distally relative to the inner member 22. Similarly, when a distal force is applied to the inner member 22 relative to the outer member 14, the inner member 22 proximally moves relative to the outer member 14. Likewise, when a proximal force is applied to the outer member 14 relative to the inner member 22, the outer member 14 proximally moves relative to the inner member 22.

As illustrated in FIGS. 1A-1E, the biopsy device 50 may further comprise a handle portion 68 operably connected to the outer member 14 and the inner member 22 and configured to provide relative axial movement of these components by the medical professional. The handle portion 68 may comprise an outer member handle portion 70 fixedly connected to the outer member 14, and an inner member handle portion 72 fixedly connected to the inner member 22. Where the inner member 22 is slidably disposed within the outer member 14, as shown in FIGS. 1A-1E, axial movement of one of the outer member handle portion 70 and the inner member handle portion 72 relative to the other axially moves one of the outer member 14 and the inner member 22 relative to the other.

The handle portion 68 may also include a marking system. The marking system may assist the medical professional gauge how far the cutting member 18 has advanced into the tissue 32, or how far the protective cap 36 is distally advanced beyond the cutting edge 26 or retracted within the cutting member 18. Generally, the marking system will assist the medical professional in determining the positions of the outer member 14 and the inner member 22 relative to each other.

An example of a handle portion is the handle of Wilson-Cook Medical, Inc.'s EchoTip® Ultra Endoscopic Ultrasound Needle.

Additionally, the biopsy device 50 may comprise at least one locking thumb screw 74 operably connected to the outer member 14 and the inner member 22 to prevent relative movement between the outer member 14 and the inner member 22 despite one of the outer member 14 and the inner member 22 being biased relative to the other. The locking thumb screw 74 may be moved between a tightened configuration and a loosened configuration. In the tightened configuration, the thumb screw 74 is engaged with the outer member 14 and the inner member 22, preventing relative movement therebetween. In the loosened configuration, the locking thumb screw 74 is disengaged from the inner member 22, enabling relative movement between the outer member 14 and the inner member 22. As shown in FIGS. 1A-1E, where the biopsy device 50 comprises a handle portion 68, the locking thumb screw 74 may be disposed on the outer member handle portion 70. The locking thumb screw is in the tightened configuration when the locking thumb screw 74 is engaged with both the outer member handle portion 70 and the inner member handle portion 72. The thumb screw 74 is one example of a mechanism that may be utilized to prevent relative movement between the outer member 14 and the inner member 22, and one of ordinary skill in the art may recognize that other types of similarly operable mechanisms may be used.

FIGS. 1A-1E illustrate one embodiment of the tissue traction mechanism 24, comprising a tissue anchor 44 attached to a suture 46. The tissue anchor 44 may be a crossbar, and is commonly referred to as a T-anchor or visceral anchor. The tissue anchor 44 may be anchored into the underlying tissue 32 using a tissue anchor delivery device, or by an anchoring means similar to that utilized by a tissue anchor delivery device. A system and method for delivering a tissue anchor delivery device to a target tissue area is disclosed in U.S. Pub. 2009-0082786-A1, and is hereby incorporated by reference. For example, a pusher 82 and a hollow needle 84 may be used to deploy the tissue anchor 44 into the tissue 32. The pusher 82 is slidably disposed within the needle 84, and the needle 84 is slidably disposed within the inner member 22. During delivery of the biopsy system 10 to the target area 12, the tissue anchor 44 is disposed within the hollow needle 84 near a distal end 86 of the needle 84, distal the pusher 82. At the target area 12, the needle 84 distally advances and pierces the tissue 32. Then, the pusher 82 distally advances and engages the tissue anchor 44, pushing the tissue anchor 44 out of the needle 84 and into the tissue 32. During delivery and deployment of the tissue anchor 44, the suture 46 attached to the tissue anchor 44 extends from the tissue anchor 44 to near a proximal end 48 of the medical biopsy system 10 so as to enable the medical professional to proximally pull on the suture 46 and withdraw the anchored tissue 32 into the cutting member 18.

FIGS. 2A-2B, and 3A-3B illustrate an alternative embodiment of the biopsy system 10, where the outer member 14 and the inner member 22 have threaded configurations. In this embodiment, the inner surface 54 of the outer member 14 and the outer surface 56 of the inner member 22 each have a helical thread disposed thereon. The outer member thread 58 and the inner member thread 60 are complimentary such that when the outer member thread 58 and the inner member thread 60 engage into each other, rotational movement of one of the outer member 14 and the inner member 22 relative to the other translates to axial movement of one of the outer member 14 and the inner member 22 relative to the other. The configuration of the thread determines the relationship between the relative rotational and axial movements.

Figure 2A:
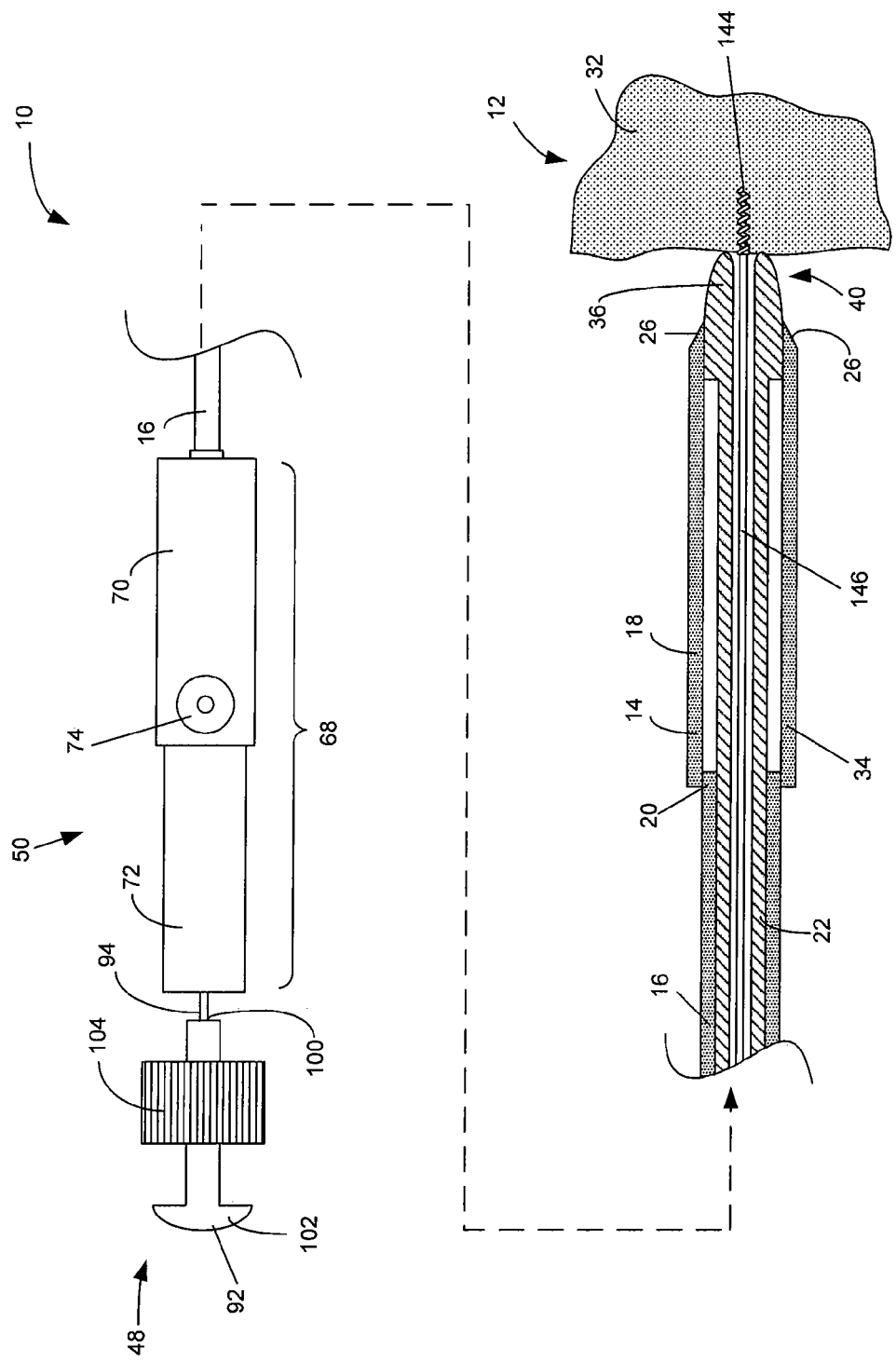
FIG. 2A is a side view of an alternative medical biopsy system, partially in cross-section, where the protective cap is positioned in the first position, and where the tissue traction mechanism comprises a stylet.
Figure 2B:
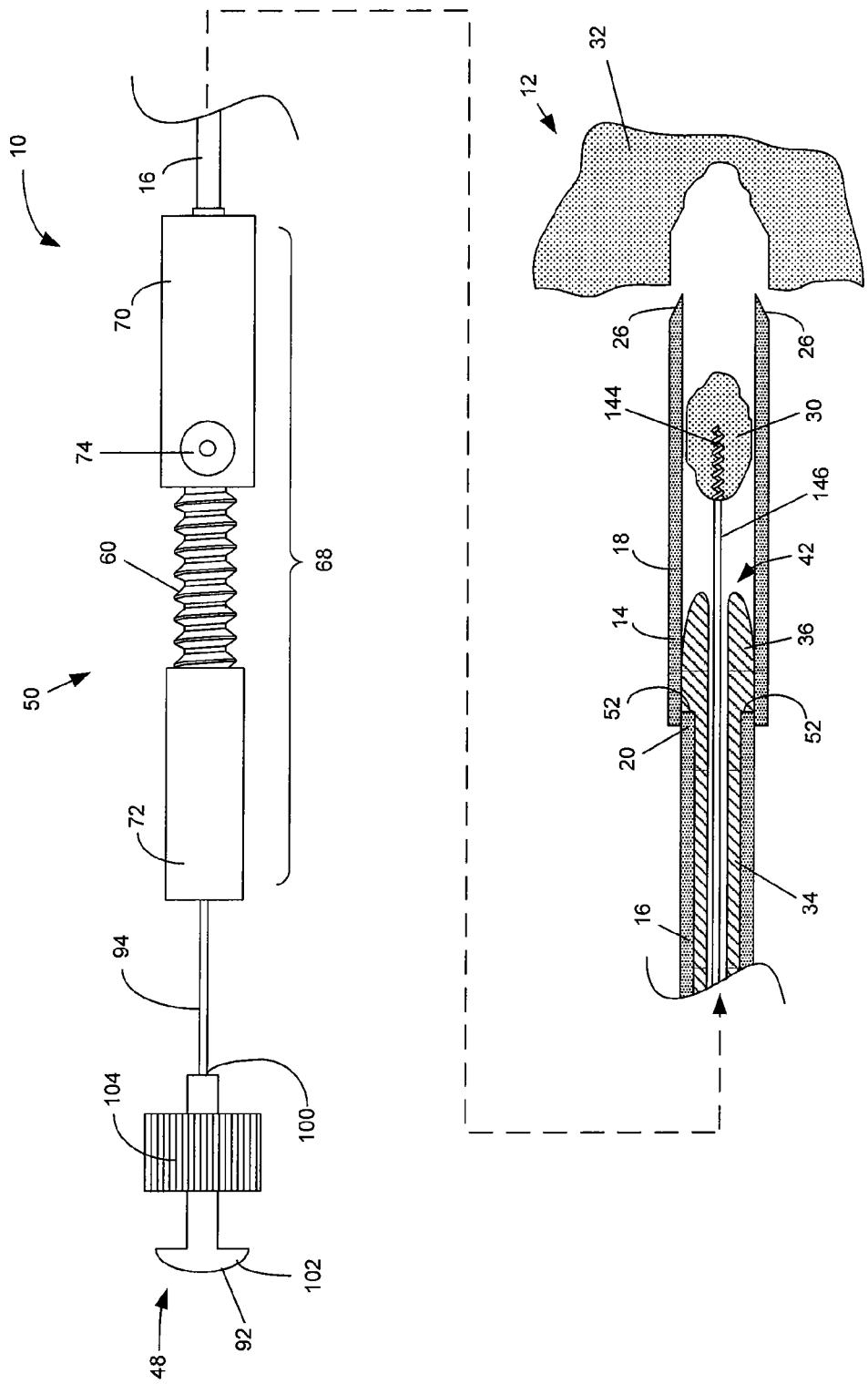
FIG. 2B is a side view of the system shown in FIG. 2A, illustrating the threaded configuration between the outer member and the inner member, where the protective cap is positioned in the second position, and where the tubular tissue sample is retracted within the cutting member.
Figure 3A:
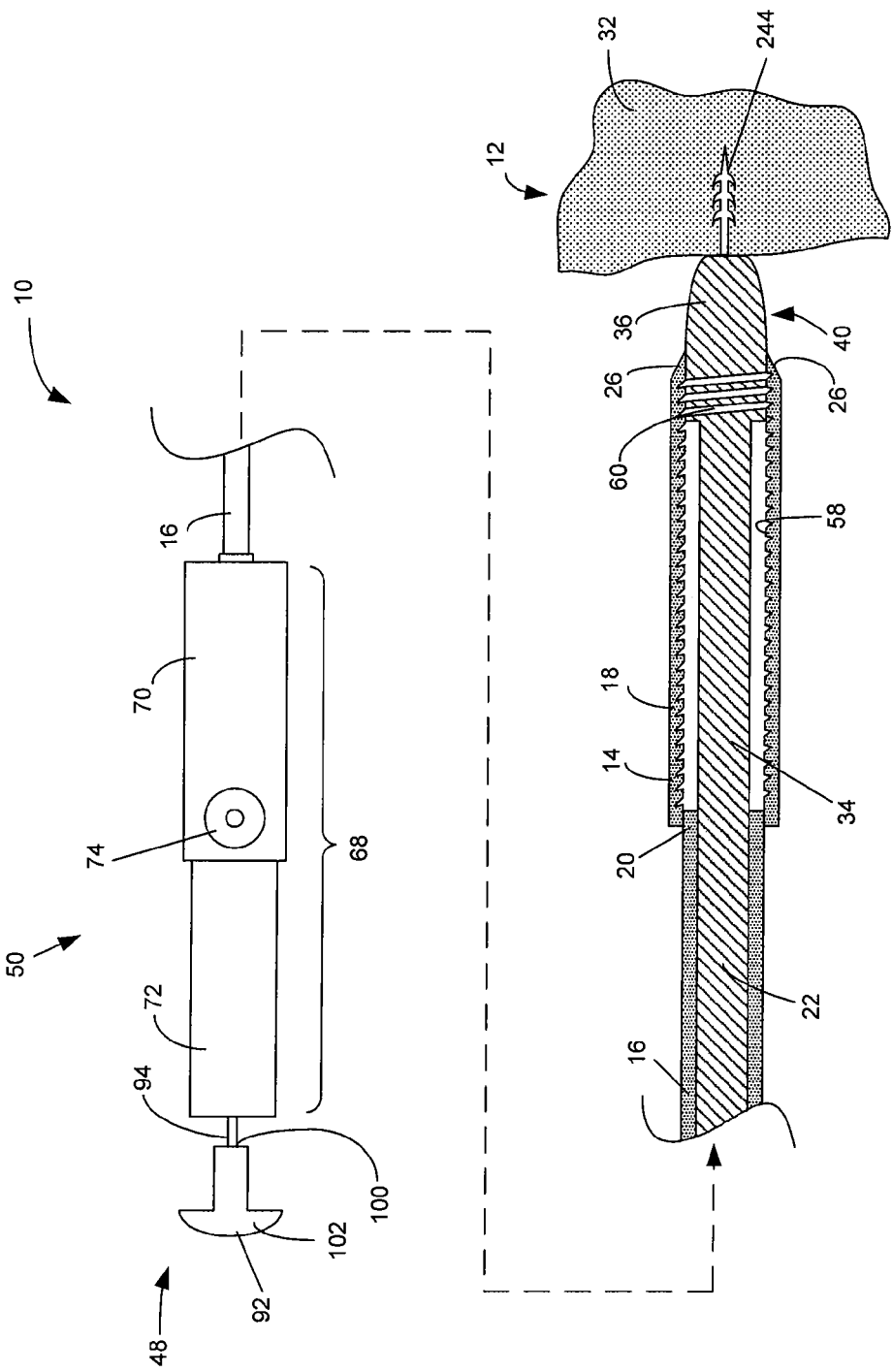
FIG. 3A is a side view of another alternative medical biopsy system, partially in cross-section, illustrating an alternative embodiment of the stylet and an alternative embodiment of the threaded configuration, and where the protective cap is positioned in the first position.
Figure 3B:
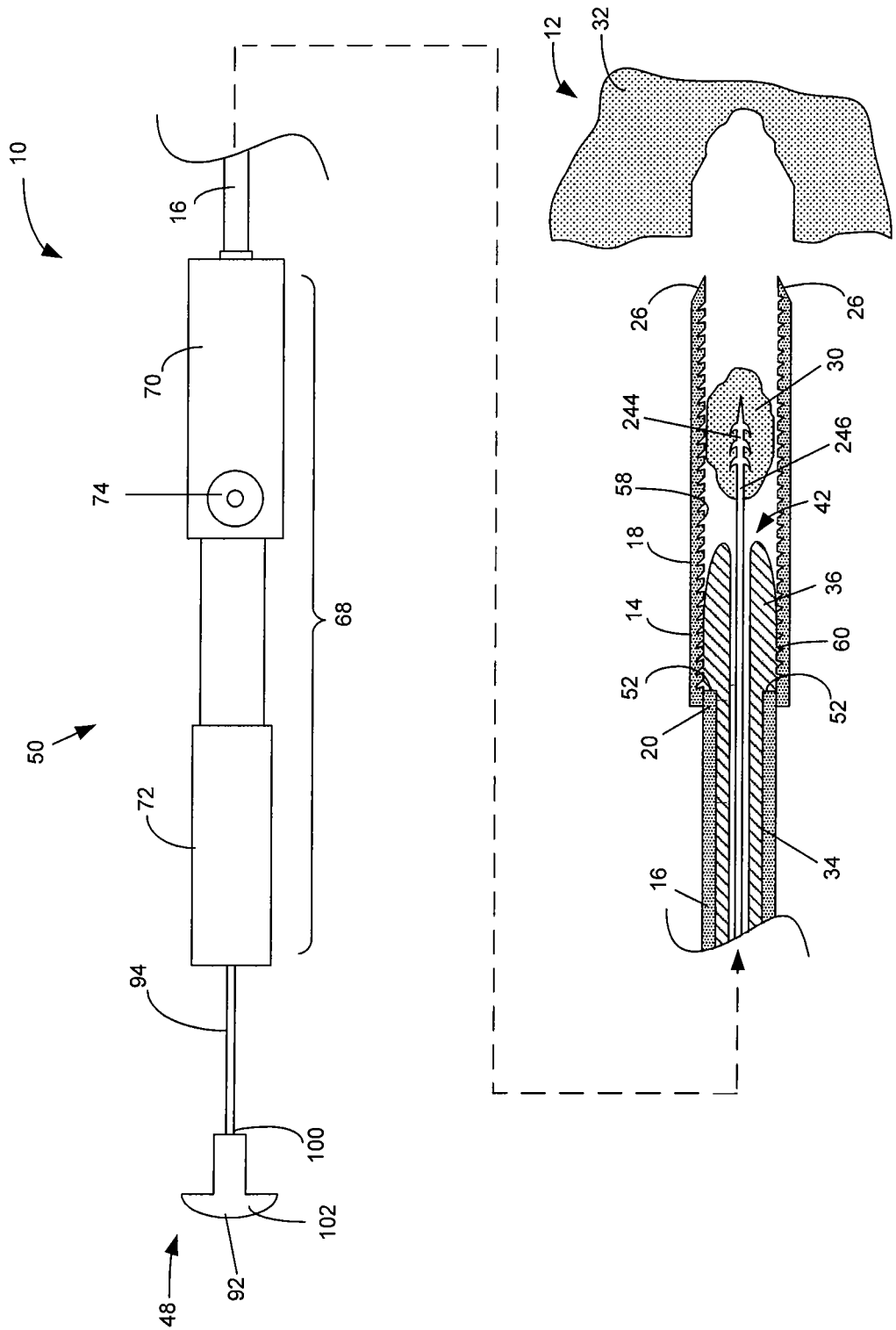
FIG. 3B is a side view of the system shown in FIG. 3A, illustrating the protective cap positioned in the second position, and the tubular tissue sample retracted within the cutting member.
Figure 4A:
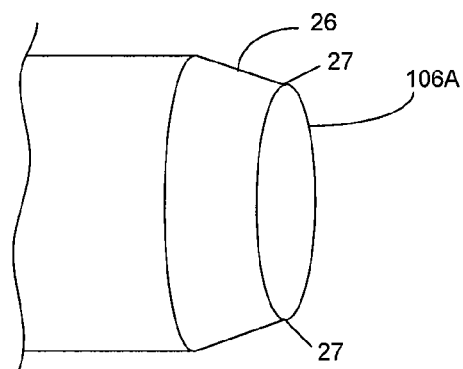
FIGS. 4A-4D are side views of the cutting edge and the various types of piercing edges.
Figure 4B:
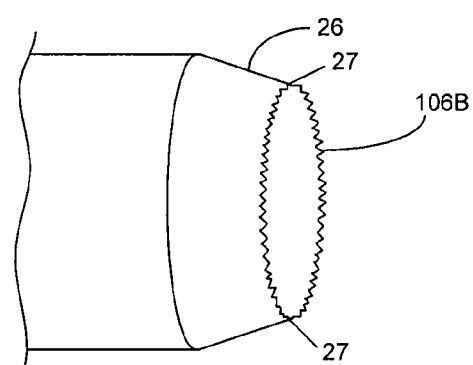
Figure 4C:
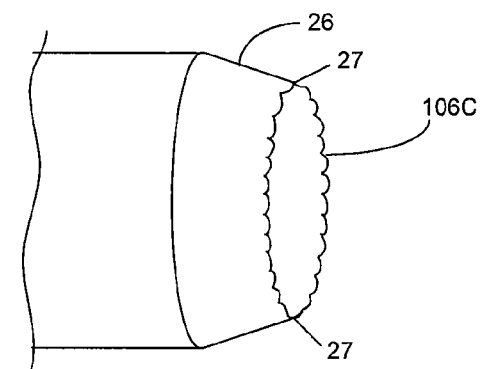
Figure 4D:
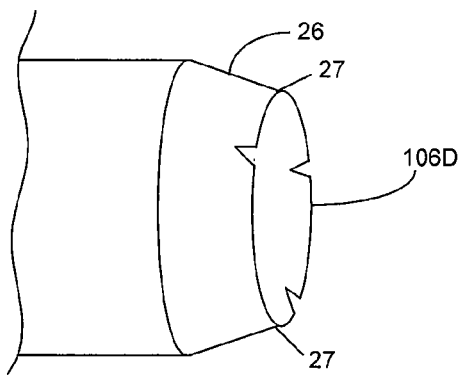

When the protective cap 36 is in the first position 40, as shown in FIGS. 2A and 3A, a rotational force may be applied (in a clockwise or counter-clockwise direction, depending on the thread configuration) to the inner member 22 relative to the outer member 14 to proximally advance the inner member 22 relative to the outer member 22 and move the protective cap 36 to the second position 42, as shown in FIGS. 2B and 3B. Alternatively, when the protective cap 36 is in the first position 40, a rotational force may be applied (in a rotational direction in accordance with the thread configuration) to the outer member 14 to distally advance the outer member 14 relative to the inner member 22. As the outer member 14 distally advances, the inner member 22 is moved to the second position 42 within the cutting member 18, as shown in FIGS. 2B and 3B.

Similarly, when the protective cap 36 is in the second position 42, as shown in FIGS. 2B and 3B, a rotational force may be applied (in a rotational direction in accordance with the thread configuration) to the inner member 22 relative to the outer member 14 to distally advance the inner member 22 to the first position 40, as shown in FIGS. 2A and 3A. Alternatively, when the protective cap 36 is in the second position 42, as shown in FIGS. 2B and 3B, a rotational force may be applied (in a rotational direction in accordance with the thread configuration) to the outer member 14 relative to the inner member 22 to proximally advance the outer member 14 relative to the inner member 22, causing the protective cap to move to the first position 40, as shown in FIGS. 2A and 3A.

In order for the protective cap 36 to be able to move between the first position 40 and the second position 42, either the outer member thread 58 or the inner member thread 60 has an axial thread length 62 at least equal to the length between the first position 40 and the second position 42. The other of the outer member thread 58 and the inner member thread 60 makes at least one revolution over the corresponding surface 54, 56. Preferably, the other of the outer member thread 58 and the inner member thread 60 has several revolutions so as to evenly displace the friction between the outer member thread 58 and the inner member thread 60 and facilitate relative rotation.

FIGS. 2A-2B and 3A-3B illustrate different configurations of the biopsy system 10 having a threaded configuration. In one configuration, as shown in FIGS. 2A-2B, the outer member thread 58 and the inner member thread 60 are disposed near the proximal end 48 of the medical biopsy system 10. Where the biopsy system 10 comprises a handle portion 68, the inner member thread is disposed on the outer surface 56 of the inner member handle portion 72, and the outer member thread 58 is disposed on the inner surface 54 of the outer member handle portion 70.

In another configuration of this embodiment, as shown in FIGS. 3A-3B, the outer member thread 58 is disposed on the inner surface 54 of the cutting member portion 18 of the outer member 14, and has an axial length equal to at least the length between the first position 40 and the second position 42. The inner member thread 60 is disposed on the outer surface 56 of the protective cap 36. These described thread dispositions are provided as examples and not limitations, and one skilled in the art would realize that the outer member thread 58 and the inner member thread 60 may comprise various axial lengths and be disposed on various locations within the inner surface 54 of the outer member 14 and the outer surface 56 of the inner member 22, respectively.

FIGS. 2A-2B and 3A-3B also illustrate alternative embodiments of the tissue traction mechanism 24. In FIGS. 2A-2B, the tissue traction mechanism 24 is a stylet 124. The style 124 comprises a rod 146 and an anchoring tip 144 having a corkscrew configuration. The corkscrewed anchoring tip 144 is disposed on a distal end thereof. A proximal portion 100 of the rod 146 extends beyond the proximal end 48 of the medical biopsy device 50. The rod 146 may comprise a stylet cap 102 disposed on the proximal portion 100 thereof. The corkscrewed anchoring tip 144 is securely anchored into the tissue 32 by simultaneously rotating and applying a distal force to the stylet 124. The rod 146 may comprise a torsion element 104 to facilitate rotation of the stylet 124.

FIGS. 3A-3B illustrate another embodiment of the tissue traction mechanism 24. In this embodiment, the tissue traction mechanism 24 is a stylet 224, comprising an anchoring tip 244 having a barbed configuration. The barbed anchoring tip 244 is securely anchored to the tissue 32 by applying a distal force to the stylet 244, which advances the barbed tip 244 into the tissue 32. The corkscrew and barbed configurations are examples to, and not limitations of, stylet anchoring tip configurations for engaging and pulling the tubular tissue sample 30 into the cutting member 18, and one skilled in the art may realize other tip configurations to mechanically retain the tissue sample 30.

FIGS. 4A-4D depict various embodiments of the cutting edge 26 circumferentially disposed about the distal end 28 of the cutting member 18. The cutting edge 26 is configured to engage and cut out the tubular tissue sample 30 from underlying tissue 32 upon rotation and distal advancement of the torsion shaft 16. The cutting edge distally terminates at a piercing point 27. A plurality of piercing points 27 concentrically disposed about a longitudinal axis comprise a piercing edge 106. The piercing edge 106 may comprise various types, including but not limited to, a plain edge 106A, a serrated edge 106B, a scalloped edge 106C, a plain edge having notches 106D, or any combination thereof that one having ordinary skill in the art may utilize to cut the tissue. Additionally, the cutting edge 26 may comprises an inwardly slanted bevel for reducing contact with an interior surface of a working channel of an endoscope through which the medical biopsy system 10 may advance.

A method for performing a tissue biopsy at a target area 12 within a patient is also provided, and is described with reference to the medical biopsy system 10 described in FIGS. 1A-1E. The method comprises advancing the biopsy device 50 to the target area 12. Preferably, an endoscope is employed and the medical biopsy system 10 is translated through the working channel of the endoscope. The endoscope also preferably includes a visualization system for assisting in locating the target area 12, and monitoring operation of the biopsy device system 10. It will be recognized that the biopsy system 10 may be delivered to the target area 12 without the use of an endoscope, and likewise other visualization techniques may be employed including catheter-based fiber optic systems, fluoroscopy, ultrasound, or the like. During advancement of the biopsy system toward the target area 12, the protective cap 36 of the inner member 22 is located in the first position 40, extending distally beyond the cutting edge 26. This configuration minimizes the contact between the cutting edge 26 and outer surroundings such as the interior of an endoscope or bodily organs.

As shown in FIG. 1A, when the biopsy system 10 reaches the target area 12, the protective cap 36 engages with the underlying tissue 32, applying tension to the tissue 32. Thereafter, the mechanical tissue anchor 44 is securely anchored in the tissue 32. To begin cutting the tissue 32, the protective cap 36 is moved proximally relative to the cutting member 18 and toward the second position 42, as shown in FIG. 1B. As the protective cap 36 is moved toward the second position 42, the cutting edge 26 is exposed and engages with the tissue 32.

As described above, the protective cap 36 may be moved from the first position 40 to the second position 42 by either proximally moving the inner member 22 relative to the outer member 14, or distally moving the outer member 14 relative to the inner member 22. FIG. 1C illustrates the first situation, where the inner member 22 is proximally moved relative to the outer member 14. In this situation, the outer member 14 remains stationary, such that the cutting edge 26 is engaged with the tissue 32, but the cutting member 18 does not advance farther into the tissue 32 while the protective cap 36 is being moved toward the second position 42. Once the protective cap is in the second position 42, the locking thumb screw may be moved to the tightened configuration to prevent relative rotational and relative axial movements between the first member and the second member. Thereafter, to cut the tissue, the biopsy device 50 is simultaneously rotated and distally advanced into the tissue 32, as shown in FIG. 1D. Alternatively, the tissue may be cut in accordance with the second situation, where the outer member 14 is moved distally relative to the inner member. In this situation, tissue 32 is cut by simultaneously rotating and distally advancing the cutting member 18 relative to the inner member. The farther the cutting member 18 is advanced into the tissue, the farther within the cutting member 18 the protective cap 36 is positioned.

As the cutting member 18 is being rotated and distally advanced into the tissue 32, the proximal end 48 of the operating member 46 is pulled, which pulls the tissue 32 into the cutting member 18, as shown in FIG. 1D. The simultaneous rotation and advancement of the cutting member 18 and the pulling of the tissue 32 causes a tubular sample 30 to be torn from the tissue 32, as shown in FIG. 1E. The tubular tissue sample 30 secured to the mechanical tissue anchor 44 may be withdrawn farther into the cutting member 18, if necessary, and the biopsy system 10 is withdrawn from the target area 12.

Where the biopsy device 50 comprises a handle 68, relative movement between the outer member 14 and the inner member 22 may be performed through operation of the handle 68. Moving the protective cap 36 from the first position 40 to the second position 42 may involve moving one of the outer member handle portion 70 and the inner handle portion 72 relative to the other. Where the inner member 22 is slidably disposed within the outer member 14, moving the protective cap 36 from first position 40 to the second position 42 may comprise proximally moving the inner member handle portion 72 relative to the outer member handle portion 70, or distally moving the outer member handle portion 70 relative to the inner member handle portion 72. Where the inner member 22 and the outer member 14 are configured in a threaded engagement, moving the protective cap 36 from the first position 40 to the second position 42 may comprise rotating one of the outer member handle portion 70 and the inner member handle portion 72 relative to the other, where the direction of the rotation depends upon the thread configuration.

The method may further comprise locking the outer member 14 and the inner member 22 in relative positions to configure the protective cap 36 in the first position 40 during advancement to and withdrawal from the target area 12, so as to prevent exposing the cutting edge 26 to the outer surroundings such as an interior surface of the endoscope. Locking the outer member 14 and the inner member 22 in relative positions may occur at any time and where the protective cap 36 is in the first position 40, the second position 42, or any position therebetween. For example, the outer member 14 and the inner member 22 may be locked in relative positions before advancing the biopsy device 50 to the target area 12 and before withdrawing the biopsy device 50 from the target area 12 once the tissue sample 30 is detached from the underlying tissue 32 and pulled within the cutting member 18. As another example, the outer member 14 and the inner member 22 may be locked before the biopsy device 50 is rotated and distally advanced into the tissue 32.

In addition, anchoring the mechanical tissue anchor 44 involves different procedures for the different tissue traction mechanisms 24, 124, 224. Where the tissue traction mechanism 24 comprises a tissue anchor 44 in connection with a suture 46, as shown in FIGS. 1A-1B, anchoring the tissue anchor 44 involves loading the tissue anchor 44 at the distal end of the hollow needle 84, distally advancing the pusher 82 through the needle 84, engaging the pusher 82 with the tissue anchor 44, and pushing the tissue anchor 44 out of the needle 84 and into the tissue 32. Where the tissue traction mechanism 24 comprises a stylet 124 having a corkscrewed anchoring tip 144, as shown in FIGS. 2A-2B, anchoring the corkscrewed tip 144 includes simultaneously rotating and distally advancing the corkscrewed anchoring tip 144 of the stylet 124 into the tissue 32. Where the tissue traction mechanism 24 comprises a stylet 224 having a barbed anchoring tip 244, as shown in FIGS. 3A-3B, anchoring the barbed tip 244 includes distally advancing the barbed tip 244 into the tissue 32.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

We claim:

1. A medical system for performing a tissue biopsy at a remote location within a patient comprising:

an elongate outer member comprising an elongate torsion shaft and a tubular cutting member disposed on a distal portion of the torsion shaft, the tubular cutting member including a cutting edge circumferentially disposed about a distal end thereof, the cutting edge configured to engage and cut out a tubular tissue sample from underlying tissue upon rotation and distal advancement of the torsion shaft;

an elongate inner member movably disposed within the outer member, the inner member comprising a shaft portion having a protective cap disposed on a distal end thereof, the protective cap movable between a first position extending distally beyond the cutting edge and a second position retracted within the cutting member to expose the cutting edge; and a tissue traction mechanism movably disposed within the inner member, the tissue traction mechanism comprising a mechanical tissue anchor connected to an operating member, wherein the tissue traction mechanism is configured to engage and pull the tubular tissue sample into the cutting member, wherein, when the cutting edge is exposed, the cutting edge is configured to engage and cut out the tubular tissue sample upon rotation and distal advancement of the torsion shaft while the tissue traction mechanism engages and pulls the tubular tissue sample in order to detach the tubular tissue sample from the underlying tissue.

2. The medical system of claim 1, wherein the medical system is configured to be movably disposed through a working channel of an endoscope; and wherein the cutting edge comprises an inwardly slanted bevel configured to reduce contact with an interior surface of the working channel.

3. The medical system of claim 1, wherein the second position is located at a proximal portion of the tubular cutting member abutting a distal end of the torsion shaft.

4. The medical system of claim 1, further comprising a handle portion operably connected to the outer member and the inner member and configured to provide axial movement therebetween; wherein the handle portion comprises an outer member handle portion fixedly attached to the outer member, and an inner member handle portion fixedly attached to the inner member.

5. The medical system of claim 1, wherein the outer member further comprises at least one locking thumbscrew operably connected to the outer member and the inner member, the at least one locking thumbscrew being configured to prevent movement of one of the outer member and the inner member relative to the other; and wherein the at least one locking thumbscrew is connected to a handle portion operably connected to the outer member and the inner member.

6. The medical system of claim 1, wherein the outer member further comprises an inner surface having a first helical thread circumferentially disposed thereon, the inner member further comprising an outer surface having a second helical thread circumferentially disposed thereon, the first thread and the second thread being configured to engage into each other such that rotational movement of one of the outer member and the inner member relative to the other axially moves one of the outer member and the inner member relative to the other.

7. The medical system of claim 6, wherein an axial length of one of the first thread and the second thread is equal to at least a length between the first position and the second position, and the other of the first thread and the second thread comprises at least one revolution over the surface of the other of the inner and the outer member.

8. The medical system of claim 7, wherein the first thread is disposed on the inner surface of the cutting member portion of the outer member, and the second thread is disposed on the outer surface of the protective cap of the shaft portion, the first thread having the axial length equal to at least the length between the first position and the second position.

9. The medical system of claim 1, wherein the mechanical tissue anchor is a crossbar, and the operating member is a suture.

10. The medical system of claim 1, wherein the tissue traction mechanism is a stylet comprising a rod having a distal tip disposed on the distal end thereof, the operating member being the rod, and the distal tip being the mechanical tissue anchor.

11. The medical system of claim 10, wherein the distal tip of the stylet has one of a corkscrew configuration and a barbed configuration.

12. The medical system of claim 1, wherein the cutting edge has one of a serrated edge configuration; a scalloped edge configuration; and at least one notch.

13. A method for performing a tissue biopsy at a remote location within a patient comprising:
    advancing a medical biopsy device comprising an outer member and an inner member to the remote location;
    engaging the bodily tissue with the device;
    anchoring the bodily tissue;
    retracting the inner member of the device relative to the outer member so as to expose and engage a cutting member disposed on the outer member with the bodily tissue; and
    rotating and distally advancing the cutting member while proximally pulling the anchored bodily tissue until a tubular tissue sample is detached from the underlying bodily tissue.

14. The method of claim 13, wherein anchoring the underlying tissue comprises deploying a tissue anchor into the underlying tissue.

15. The method of claim 14, wherein anchoring the underlying tissue comprises inserting a distal anchoring tip of a stylet into the bodily tissue.

16. The method of claim 15, wherein the distal anchoring tip of the stylet comprises one of a corkscrew configuration and a barbed configuration, and inserting the distal end of the stylet comprises distally advancing the one of the corkscrew configuration and the barbed configuration.

17. The method of claim 16, wherein the distal anchoring tip of the stylet comprises a barbed configuration, and inserting the distal end of the stylet comprises distally advancing the barbed anchoring tip.

18. The method of claim 14, wherein retracting the inner member of the device relative to the outer member so as to expose and engage the cutting member with the bodily tissue comprises moving one of a first handle portion fixedly attached to the outer member and a second handle portion fixedly attached to the inner member relative to the other.

19. The method of claim 18, wherein moving one of the first handle portion and the second handle portion relative to the other comprises rotating about a longitudinal axis the first handle portion relative to the second handle portion.

20. The method of claim 14, further comprising retracting the sample tissue into the cutting member, wherein retracting the sample tissue into the cutting member comprises pulling in a proximal direction a suture attached to a crossbar.

21. The method of claim 14, further comprising retracting the sample tissue into the cutting member, wherein retracting the sample tissue into the cutting member comprises withdrawing in a proximal direction a stylet that is anchoring the tissue sample.

22. A medical system for performing a tissue biopsy at a remote location within a patient comprising:
    an elongate outer member comprising an elongate torsion shaft and a tubular cutting member disposed on a distal portion of the torsion shaft, the tubular cutting member including a cutting edge circumferentially disposed about a distal end thereof, the cutting edge configured to engage and cut out a tubular tissue sample from underlying tissue upon rotation and distal advancement of the torsion shaft;
    an elongate inner member movably disposed within the outer member, the inner member comprising a shaft portion having a protective cap disposed on a distal end thereof, the protective cap movable between a first position extending distally beyond the cutting edge and a second position retracted within the cutting member to expose the cutting edge; and
    a tissue traction mechanism movably disposed within the inner member, the tissue traction mechanism comprising a mechanical tissue anchor connected to an operating member, wherein the tissue traction mechanism is configured to engage and pull the tubular tissue sample into the cutting member,
    wherein the protective cap comprises a rounded end to engage with the underlying tissue prior to engagement and pulling of the tubular tissue sample into the cutting member with the tissue traction mechanism.

* * * * *